(12) United States Patent
Berkcan et al.

(10) Patent No.: US 7,276,703 B2
(45) Date of Patent: Oct. 2, 2007

(54) SYSTEM TO MONITOR THE HEALTH OF A STRUCTURE, SENSOR NODES, PROGRAM PRODUCT, AND RELATED METHODS

(75) Inventors: Ertugrul Berkcan, Clifton Park, NY (US); Emad Andarawis, Ballston Lake, NY (US); Robert Wojnarowski, Ballston Lake, NY (US)

(73) Assignee: Lockheed Martin Corporation, Bethesda, MD (US)

( * ) Notice: Subject to any disclaimer, the term of this patent is extended or adjusted under 35 U.S.C. 154(b) by 0 days.

(21) Appl. No.: 11/287,009

(22) Filed: Nov. 23, 2005

(65) Prior Publication Data
US 2007/0114422 A1    May 24, 2007

(51) Int. Cl.
*G01F 23/00*    (2006.01)
(52) U.S. Cl. .................................. 250/358.1; 307/112
(58) Field of Classification Search ............. 250/358.1, 250/458.1, 459.1, 461.1; 307/112
See application file for complete search history.

(56) References Cited
U.S. PATENT DOCUMENTS

| | | | |
|---|---|---|---|
| 5,440,300 A | 8/1995 | Spillman, Jr. | |
| 6,563,122 B1 * | 5/2003 | Ludeker et al. | 250/458.1 |
| 6,564,640 B1 | 5/2003 | Allaei | |
| 7,081,693 B2 * | 7/2006 | Hamel et al. | 307/151 |
| 7,110,880 B2 * | 9/2006 | Breed et al. | 701/207 |
| 2003/0234730 A1 | 12/2003 | Arms et al. | |
| 2004/0078662 A1 * | 4/2004 | Hamel et al. | 714/22 |
| 2005/0017602 A1 | 1/2005 | Arms et al. | |

* cited by examiner

*Primary Examiner*—David Porta
*Assistant Examiner*—Marcus Taningco
(74) *Attorney, Agent, or Firm*—Bracewell & Giuliani LLP (57) ABSTRACT

A system to monitor the health of a structure, sensor nodes, program product, and associated methods are provided. The system includes an array of health monitoring sensor nodes connected to or embedded within a structure to monitor the health of the structure. The health monitoring sensor nodes include sensor elements positioned to sense parameters of the structure and to provide data related to the parameters to a health monitoring sensor node data collector. The sensor nodes can each include an energy harvester to harvest energy to power the sensor node. The system also includes an energy distributing node positioned to provide energy to the sensor nodes, through the structure being monitored, to be harvested by energy harvester of the sensor nodes.

30 Claims, 6 Drawing Sheets

SYSTEM TO MONITOR THE HEALTH OF A STRUCTURE, SENSOR NODES, PROGRAM PRODUCT, AND RELATED METHODS

RELATED APPLICATIONS

This invention is related to Non-Provisional application Ser. No. 11/286,795, by Andarawis, et al., titled "System to Monitor the Health of a Structure, Sensor Nodes, Program Product, and Related Methods", filed on Nov. 23, 2005, and Non-Provisional application Ser. No. 11/286,792, by Andarawis, et al., titled "System to Monitor the Health of a Structure, Sensor Nodes, Program Product, and Related Methods," filed on Nov. 23, 2005, all incorporated by reference herein in their entirety.

BACKGROUND OF THE INVENTION

1. Field of the Invention

The present invention relates generally to multi-node sensor systems. More specifically, the present invention relates to a system, sensor nodes, program product, and related methods to monitor the health of structural components and to deliver power to distributed sensor nodes.

2. Description of the Related Art

Various types of platforms such as, for example, aircraft structural components, aircraft skins, or other related components, when in operation are subjected to various environmental conditions such as stress and strain, exposure to temperature extremes, and/or significant vibration energy. Due to the various environmental conditions such components can suffer material degradation over time.

Structural health monitoring helps promote realization of the full potential of such components. Remotely position sensors (nodes) have been installed adjacent to such structures/components to monitor various parameters such as, for example, strain levels, stress, temperature, pressure, or vibration level to help manage physical inspection schedules, maintenance schedules, to help predict material failure, and generally monitor the "health" of such components. Such sensors have been provided a dedicated power supply such as power obtained through conductors, e.g., wires, connected to the aircraft electrical system or through chemical batteries. Such wiring can undesirably result in increased weight and complexity of the component being monitored and/or the associated structure, and are subject to damage or breakage requiring extensive repair costs and down time. Depending upon available space, batteries can be inappropriate due to their size. Batteries can also have a limited service life and, therefore, typically require periodic inspection and/or replacement, are often positioned in locations difficult to reach, and often require costly disassembly and reassembly of the sensor or component to perform service on the battery. Further, batteries may not be suitable due to environmental constraints, i.e., temperature changes often affect battery performance.

Some more recent structural health monitoring systems include sensors connected to a network of fiber-optic conductors to form an interrogation system. Such fiber-optic conductors, as with electrical conductors, can significantly raise the complexity of the component and/or deployment the sensor system. Other structural health monitoring systems include self-powered sensors attached to or embedded within the components to be monitored that can reduce dependence on batteries or any other external power source. Such sensors can be relatively small in size and can utilize the energy translated through the component being monitored as a power source. Such devices can include those known as micro-electro-mechanical systems (MEMS). This type of sensor can typically consume very low amounts of power in the microwatt range. Such devices can include those known as piezoelectric devices. Some related piezoelectric devices can be in the form of actuators which can to apply a force on the associated structure to dampen detected vibrations. That is, such actuators can selectively inject directed vibrations to cancel existing undesired vibrations or noise.

Both of the foregoing example types of sensors can generate small electrical currents when, for example, the material is deflected, such as when the monitored component vibrates. Further, both of these types of sensors can include a storage element such as a capacitor to supplement power requirements. Such devices, however, must be positioned in both those areas having a high level of environmental energy and also in areas having a low level of environmental energy to provide sufficient monitoring capability. Because power harvesting relies on energy being available in the vicinity of the power harvesting portion of the sensor, even with the inclusion of a separate storage element, the sensors positioned in the areas of low environmental energy often do not receive sufficient power to provide continuous sensing capability necessary to perform even sampled sensing having a small duty cycle. Correspondingly, such environmental energy limitation often imposes a constraint on where the sensors can be located and thus, the adequacy of using such sensors. Additionally, the available energy distribution may change such that an area once having a high level of environmental energy now is subject only to a low-level of such energy, making power availability less reliable.

Still other health monitoring systems include wireless sensors that receive energy to retrieve sensed data from, for example, a mobile vehicle or to handheld base device which transmits a signal to each wireless sensor positioned on or in the monitored component or structure, to power or recharge the sensors. Typically an operator positions the base device adjacent the various sensors to power the sensors to thereby receive sensor data. With respect to a moving structure, however, such as, for example, an aircraft or other vehicle in operation, this type of device does not provide power to sensors that utilize a near field communication scheme.

In view of the foregoing, it would be desirable to provide a self-powered sensor system that reduces dependence on batteries or any other external power source that can include sensors capable of harvesting energy from areas of high environmental energy and provide power to those sensors in areas of low environmental energy.

SUMMARY OF THE INVENTION

In view of the foregoing, embodiments of the present invention advantageously provide a health monitoring system that reduces dependence on batteries or any other external power source, providing a combination of power harvesting and radiated power to enhance wireless power distribution in a multi-node system. Embodiments of the present invention advantageously provide a health monitoring system that includes sensor nodes capable of harvesting energy from areas of high environmental energy and/or providing power to those sensor nodes located in areas that may not be in an optimal location for environmental energy harvesting, e.g., those positioned in an area of low environmental energy.

More specifically, in an embodiment of the present invention, a system to monitor the health of a structure that can convert and distribute (redistribute) excess energy to a plurality of energy harvesting structural health monitoring sensor nodes includes a structure to be monitored having a body including an area of high environmental energy and an area of low environmental energy when in operation. For example, the structure can include an aircraft having a portion of the fuselage aft of the engine exhaust subjected to a large quantity of heat energy and a portion of the fuselage forward of the engine subjected to little or no heat energy other than that of the ambient air. The system can also include a plurality of health monitoring sensor nodes connected to or embedded within the body of the structure. For example, an aircraft skin, to monitor data related to various parameters of interest. Such parameters of interest can include, for example, temperature, pressure, strain, which is preferably temperature compensated, and acceleration including vibration levels. As many as twenty to thirty or more health monitoring sensor nodes per square foot can be positioned throughout strategic locations along the body of the structure.

The health monitoring sensor nodes can include a processor in communication with one or more sensor elements adapted to sense the various parameters of interest, and volatile and/or nonvolatile memory coupled to the processor to store operating instructions and to store data related to the parameters of interest. The health monitoring sensor nodes can also include an antenna arrangement to provide data related to the various parameters of interest to a data collector and/or central processor to compile the collected data to provide for both monitoring and managing the health of the structure. The health monitoring sensor nodes can also include an energy harvester positioned to harvest energy provided by mechanical, chemical, heat, solar, or other means including acoustic energy, radiofrequency energy, electromagnetic energy, optical (light) or solar energy, thermal energy, and vibration energy.

The system can also include one or more energy distributing nodes connected to the body of the structure to distribute or radiate energy to a subset of the health monitoring sensor nodes. The energy distributing nodes can include an energy transmitter or distributor to provide energy through the body of the structure to each of the energy harvesting health monitoring sensor nodes. The type of energy transmitter or distributor is dependent upon the type of energy to be transferred. For example, depending upon the type of material of the structure to be monitored and the position of the health monitoring sensor nodes, the energy to be transmitted or distributed can be in the form of one or more of the following: acoustic energy, radiofrequency energy, electromagnetic energy, optical (light) energy, thermal energy, and vibration energy. Correspondingly, the energy transmitter or distributor can be an acoustic, radiofrequency, electromagnetic, optical, thermal, or vibration (mechanical) distributor, respectively.

The energy distributing nodes can also include an energy harvester to harvest energy and an energy storage circuit or device to store some of the harvested energy. As such, the energy distributing nodes can be positioned in the area of high environmental energy to thereby obtain environmental energy from the body to power the energy distributing node and to convert and distribute excess energy to the energy harvesting health monitoring sensor nodes positioned in the area of low environmental energy. For example, in an environment with a high rate of mechanical motion such as in an aircraft or other vehicle, mechanical energy, e.g., vibrations caused by the aircraft engines and wind stresses can be easily tapped.

In alternative embodiments of the present invention, the energy distributing nodes can include a chemical battery or other storage device or can be in communication with an external power supply to provide power to the adjacent health monitoring sensor nodes. Regardless of the configuration, the energy harvester of each health monitoring sensor node can utilize a portion of the distributed energy to function where power levels would otherwise be insufficient without the additional power provided by the energy distributing nodes.

BRIEF DESCRIPTION OF THE DRAWINGS

So that the manner in which the features and advantages of the invention, as well as others which will become apparent, may be understood in more detail, a more particular description of the invention briefly summarized above may be had by reference to the embodiments thereof which are illustrated in the appended drawings, which form a part of this specification. It is to be noted, however, that the drawings illustrate only various embodiments of the invention and are therefore not to be considered limiting of the invention's scope as it may include other effective embodiments as well.

DETAILED DESCRIPTION

The present invention will now be described more fully hereinafter with reference to the accompanying drawings, which illustrate embodiments of the invention. This invention may, however, be embodied in many different forms and should not be construed as limited to the illustrated embodiments set forth herein. Rather, these embodiments are provided so that this disclosure will be thorough and complete, and will fully convey the scope of the invention to those skilled in the art. Like numbers refer to like elements throughout. Prime notation, if used, indicates similar elements in alternative embodiments.

Multi-node health monitoring sensor systems require that each node be powered to perform the sensing function. In wireless structural health monitoring applications where batteries are not appropriate due to their size, longevity, or environmental constraints, or when it is desired to supplement batteries with alternate energy sources to achieve long operating life, power harvesting techniques are employed. Because power harvesting relies on energy being available in the vicinity of the power harvesting portion of the sensor nodes, placement of the sensor nodes can be restricted or constrained to areas having sufficient environmental energy. Further, environmental energy distribution may change making power availability less reliable where the sensors are fixedly positioned on or within a structure. Thus, advantageously, as illustrated in FIGS. 1-11, embodiments of the present invention provide a system, sensor nodes, program product, and methods to distribute excess energy to a energy harvesting health monitoring sensor nodes positioned in areas of low or insufficient environmental energy.

Figure 1:
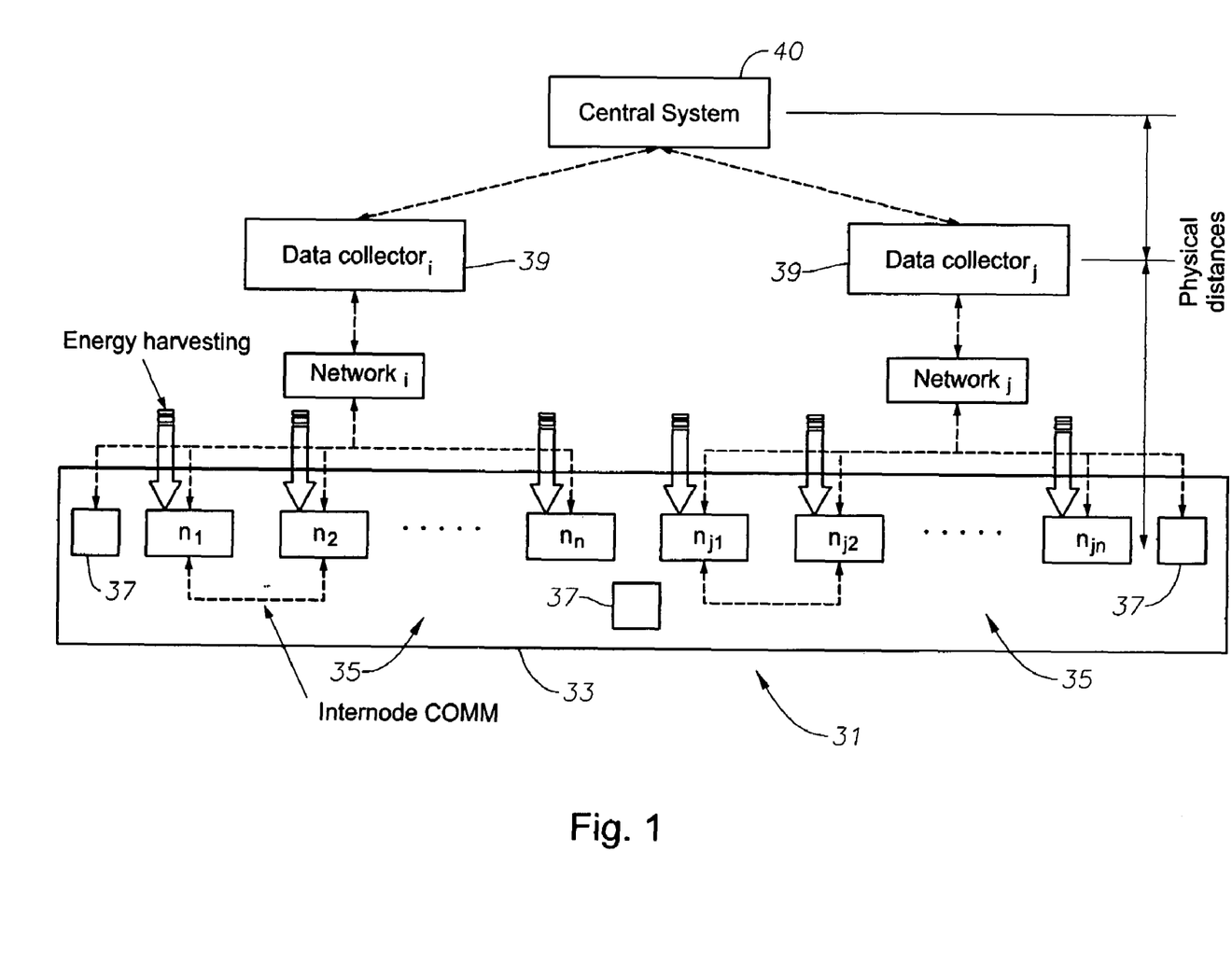
FIG. 1 is a schematic diagram of a general system architecture of a system to monitor the health of a structure according to an embodiment of the present invention.

As perhaps best shown in FIG. 1, a system 30 to monitor the health of a structure that can convert and distribute (redistribute) excess energy to a plurality of energy harvesting health monitoring sensor nodes includes a structure 31 having a body 33 or portion thereof to be monitored. Examples of such body 33 can include the leading-edge, a joint, or the skin of an aircraft wing, an aircraft fuselage, various structural parts of other vehicles subject to environmental forces, and the support beams of stationery structures such as bridges, just to name a few. In general, the system 30 includes a plurality of energy harvesting health monitoring sensor nodes 35 positioned to monitor the health of the structure, one or more energy distributing nodes 37 positioned to provide energy to neighboring health monitoring sensor nodes 35, one or more data collectors 39 or interrogators positioned or positionable to supply power to and receive data from each of the health monitoring sensor nodes 35, and a central processor, computer, or other interrogation apparatus 40 to compile the collected data to provide for both monitoring and managing the health of the structure 31.

Figure 2:
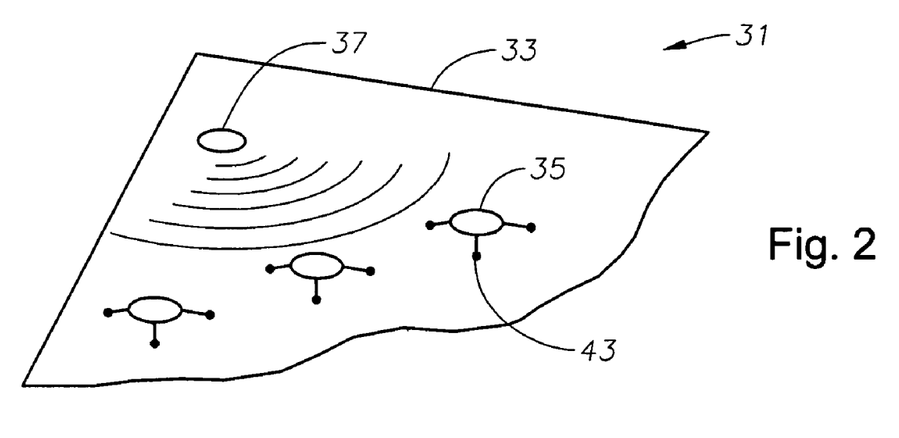
FIG. 2 is a partial environmental view of a system to monitor the health of a structure according to an embodiment of the present invention.

More specifically, as shown in FIG. 2, the system. 30 includes a plurality of health monitoring sensor nodes 35, connected to or embedded within, for example, the aircraft skin, to monitor data related to various parameters of interest. Such parameters of interest can include, for example, temperature, pressure, acceleration including vibration levels, and strain, which is preferably temperature compensated. According to various embodiments of the present invention, as many as twenty to thirty or more health monitoring sensor nodes 35 per square foot can be positioned throughout strategic locations along an, e.g., aircraft or other structure 31. Each health monitoring sensor node 35 can be in the form of an energy harvesting health monitoring sensor node capable of harvesting energy from the environment.

Each health monitoring sensor node 35 can include a processor 41 (see, e.g., FIG. 3) in communication with one or more sensor elements 43 connected to the processor 41 typically through either an electrical or a fiber-optic conductor, or can be built into the main body of the node 35. Each sensor element 43 is adapted to sense the various parameters of interest. Each sensor element 43 can be in the form of a strain gage, temperature sensor, pressure sensor, accelerometers, acoustic receiver, or other form of sensor known to those skilled in the art. Each health monitoring sensor node 35 can support one or more sensor elements 43 having either the same form or each having a separate form. For example, in order to provide temperature compensated strain, one sensor element 43 can be a piezoelectric strain gage, while the other can be a temperature sensor.

Figure 3:
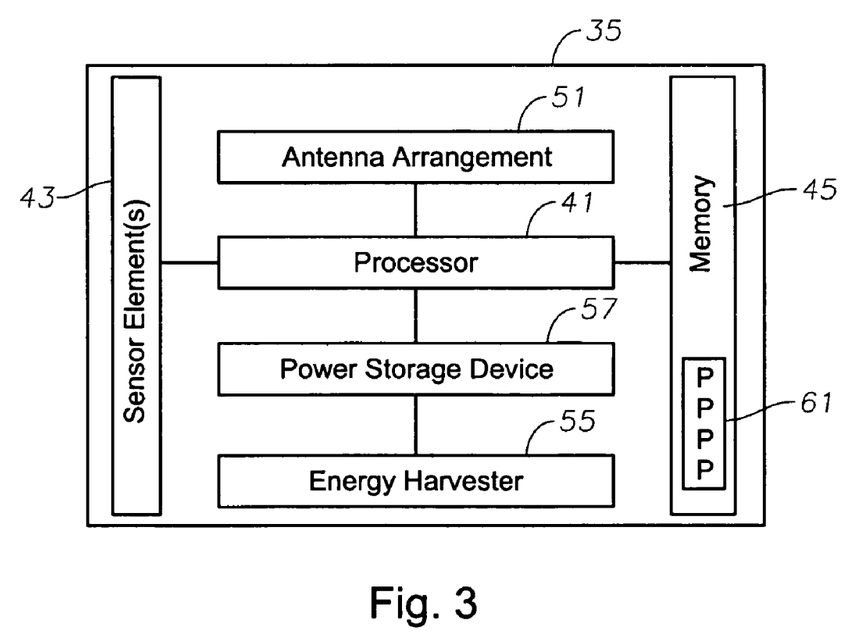
FIG. 3 is a schematic diagram of a health monitoring sensor node configured to sense parameters and to harvesting energy from a structure according to an embodiment of the present invention.

As shown, for example, in FIG. 3, each health monitoring sensor node 35 can also include volatile and/or nonvolatile memory 45 coupled to the processor 41 to store operating instructions and to store data related to the parameters of interest. Such data can be in the form of either raw sensor data or a reduced form of the data such as, for example, a data structure summarizing the raw sensor data or summarizing information analyzed from the raw data. If the data from the sensor elements 43 is supplied in an analog form, a signal processor (not shown) located within or external to the processor 41 can be used to digitize the data for use by the processor 41.

Each health monitoring sensor node 35 can also include a radiofrequency antenna, transceiver, acoustic or optical transceiver, or other form of communication arrangement such as, for example, the illustrated antenna arrangement 51, coupled to the processor 41 to receive power and interrogation signals from a data collector 39 or other dependent or independent form of health monitoring sensor node interrogator. For radiofrequency communication schemes, the antenna arrangement 51 can be in the form of various circuit elements known to those skilled in the art such as, for example, a transceiver, LC tank circuit, or other telemetry circuit. According to one embodiment of the present invention, the antenna arrangement 51 can take the form of and provide data according to methodologies described in a co-pending U.S. Non-Provisional patent application Ser. No. 11/286,792 by Andarawis, et al. also titled "System to Monitor the Health of Structural Components, Sensor Nodes, Program Product, and Related Methods" filed on Nov. 23, 2005, incorporated herein by reference in its entirety. As shown in FIG. 1, one or more data collectors 39 or other health monitoring sensor node interrogators can be provided to interrogate each set of a plurality of health monitoring sensor nodes 35. According to various embodiments of the present invention, the data collectors 39 can be handheld, fixed to the aircraft at various strategic locations, and/or positioned within a fixed facility, e.g., hangar, to read the health monitoring sensor nodes 35 when the structure 31, e.g., aircraft or aircraft wing, is passed through a gate or when parked in a parking location.

Each health monitoring sensor node 35 can also include an energy harvester 55 known and understood by those skilled in the art. The energy harvester 55 can harvest energy provided by mechanical, chemical, heat, solar, or other means including acoustic energy, radiofrequency energy, electromagnetic energy, optical (light) or solar energy, thermal energy, and vibration, or other mechanical energy. In, for example, an environment with a high rate of mechanical motion such as in an aircraft, mechanical energy, e.g., vibration energy caused by the aircraft engines and wind stresses can be easily tapped. Correspondingly, the energy harvester 55 can include, for example, a piezoelectric device or similar device known to those skilled in the art to harvest acoustic or vibration energy received as an acoustic or vibratory signal to convert the harvested acoustic or vibration energy to electrical energy, to thereby provide power to the sensor node 35.

The energy harvester 55 can alternatively include an electromagnetic energy receiver positioned to harvest electromagnetic energy to convert the harvested electromagnetic energy to electrical energy, to thereby provide power to the sensor node 35. In, for example, an aircraft, electromagnetic energy such as, for example, microwave energy, is generally readily available due to leakage from the aircraft radar. Similarly, the energy harvester 55 can alternatively include a radiofrequency receiver or similar device known to those skilled in the art including, e.g., a combination of an antenna and receiver circuit such as an LC tank or other similar circuit, to harvest radiofrequency energy received as a radiofrequency signal and to convert the harvested radiofrequency energy to electrical energy, to thereby provide power to the sensor node 35. Again, in the aircraft example, large quantities of radiofrequency energy are frequently available along portions of the body 33 of the structure 31 adjacent radio antennas and navigation antennas.

The energy harvester 55 can alternatively include an optical receiver or similar device known to those skilled in the art, e.g., photovoltaic cell, to harvest optical energy generally in the form of either solar energy or a light signal provided by a light emitting diode or incandescent bulb, to convert the harvested portion of the optical signal to electrical energy, to thereby provide power to the sensor node. In the aircraft example, optical energy is readily available at the aircraft surface during daylight hours, and adjacent the various types of aircraft lighting, some of which are on for the duration of a flight.

The energy harvester 55 can also alternatively include a thermal energy receiver or other similar device known to those skilled in the art to harvest thermal energy, e.g., a thermal coupler, to convert the harvested portion of the thermal energy to electrical energy, to thereby provide power to the sensor node. Again, in the aircraft example, thermal energy is readily available from various sources such as, for example, waste heat from the engine exhaust, heat from the engine casing, heat generated from friction with the atmosphere, and residual heat from various electrical components including communication, navigation, and lighting equipment.

The health monitoring sensor nodes 35 can include a combination of one or more of the various forms of energy harvester 55, such as those described above, to thereby maximize extracting environmental or non-environmental provided energy. For example, one or more of the health monitoring sensor nodes 35 can include the acoustic or vibration harvesting device, e.g. piezoelectric device, to extract energy from a first frequency range, and can include a second vibration energy harvester to harvest a portion of the vibration energy distributed from another energy source having a second frequency range. Note, according to embodiments of the present invention, such one or more sensor elements 43 and the mechanism of the energy harvester 55 can advantageously be the same device. For example, a vibration sensor element can also take the form of an energy harvester positioned to harvest energy of the sensed vibrations. Similarly, a temperature sensor element can also take the form of an energy harvester positioned to harvest sensed heat energy.

Regardless of the configuration, effectively, the energy harvester 55 generally can be substantially constantly producing electrical power during operation of the aircraft because the mechanism of the energy harvester is constantly being stressed by the various environmental stresses. Depending upon the configuration, this power is made available to the various components of the health moderate sensor node 35 including the processor 41, sensor element or elements 43, memory 45, antenna arrangement 51, a clock or timing device if separate from the processor 41, and/or a power storage circuit or device, e.g. device 57, to store power received through the energy harvester 55. Note, according to an embodiment of the present invention, the power storage device 57 can include a capacitor and a power signal conditioning circuit known to those skilled in the art such as, for example, a bridge rectifier. According to another embodiment of the present invention, the power storage device 57 can also or alternatively include a chemical battery.

Specific parameters of the structure 31 are measured by the sensor elements 43 and passed to the processor 41, which can either manipulate the data, store the data in the memory 45, provide the parameter data or a representation thereof (collectively "data") to the antenna arrangement 51 for transmission if utilizing an active communication scheme, and/or await a signal from a data collector or interrogator to provide such data. The data can be provided for relayed to the central processor, computer, or other interrogation apparatus 40 for further processing, in response to a request for the data, to provide for both monitoring and managing the health of the structure 31.

According to embodiments of the present invention utilizing a passive communication scheme, the communication or antenna arrangement 51 of each health monitoring sensor node 35 can be configured for near field communications. According to such passive scheme, in an embodiment of the present invention, a request for data can take the form of providing a signal having a preselected frequency and/or obtaining a certain level of stored energy from such signal. In the illustrated example, in response to such a request, the node or nodes 35 can enable communication by tuning the receiving antenna and/or the load across a receiving antenna using an inductive or backscattering coupling scheme. The data collector or other interrogator 39 senses the change in load or resonant frequency to receive data from each node 35. A relatively low frequency of, for example, between 100 to 150 kHz, preferably 125 kHz, can be used when the portion of the structure 31 interfaced with the nodes 35 includes conductive or other such material such as, for example, carbon fiber, which may significantly attenuate communication signals at higher frequencies. If utilizing an active communication scheme, the request can typically take the form of a direct interrogation of the each node 35, including or simultaneously, followed by a direct transmission of the data using stored and/or harvested energy. Further, in an active communication scheme, depending on a variable energy, the nodes 35 can form a network, such as a wireless hierarchal or mesh network, to relay such data to the data collector or other interrogator 39.

According to embodiments present invention, one or more of the energy harvesting health monitoring sensor nodes 35 can receive a signal from and provide data to the interrogator 39 using a media such as, for example, electromagnetic, acoustic, and optical, having a first tuned or otherwise selected to enhance data transmission efficiency. Further, rather than utilize the same media or media having the same frequency, the energy harvester 55 can be tuned to or otherwise set at a second frequency to provide for substantial energy conversion efficiency. For example, with respect to the node 35 illustrated in FIG. 3, the antenna arrangement 51 can receive a signal from and provide data to an interrogator 39 using a first preselected resonant frequency tuned to provide for substantial transmission energy efficiency based upon a material composition of the body 33 of the structure 31. The energy harvester 55 can correspondingly be in the form of a second antenna arrangement tuned to a second preselected resonant frequency and positioned to harvest energy to provide for substantial energy conversion efficiency, which is dependent upon the material composition of the body 33 of the structure 31. That is, e.g., the second frequency utilized by the energy harvester 55 can be in the form of low frequency radiofrequency energy which is typically less attenuated by, e.g., carbon fiber structures than that of higher frequencies typically used in communications. Similarly, with respect to an acoustic signal, various material properties also can dictate which frequencies are more or less attenuated. Also for example, with respect to optics, some materials can be transparent to optical energy, e.g., in the infrared spectrum, but can be completely opaque to that of visible light, or can have differing reflective, refractive, or scatter properties.

According to embodiments of the present invention, as perhaps best shown in FIG. 3, rather than providing an individually tailored circuit arrangement, each health monitoring sensor node 35 can be implemented such that the processor 41 has operating instructions and/or parameter processing program product 61 stored in the memory 45 which includes instructions that when executed by the processor 41 perform the various operations, described above. Note, the program product 61 can be in the form of microcode, programs, routines, and symbolic languages that provide a specific set or sets of ordered operations that control the functioning of the hardware and direct its operation, as known and understood by those skilled in the art.

Figure 4:
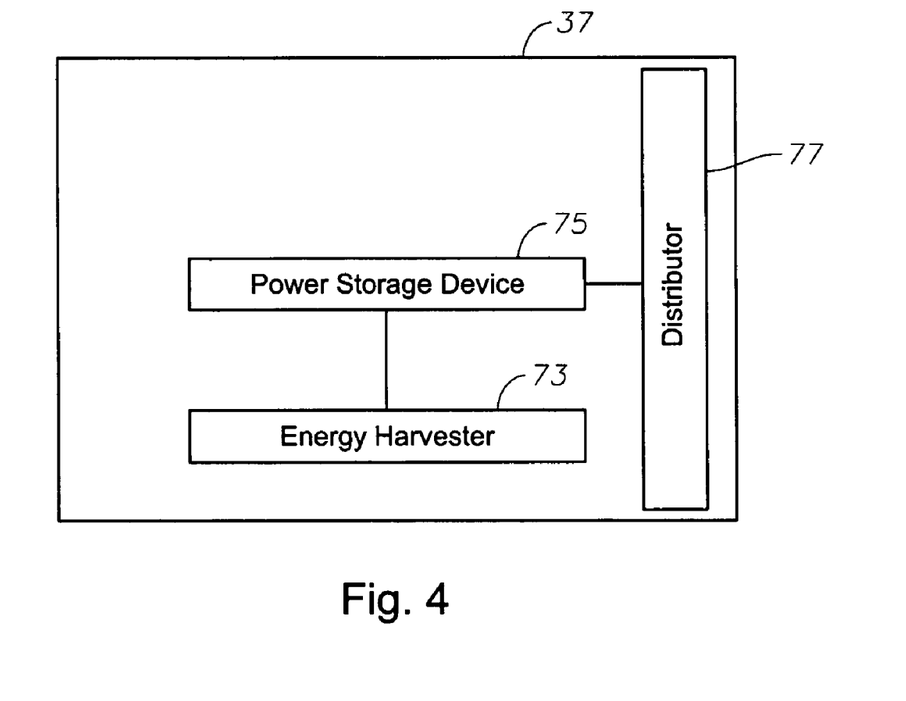
FIG. 4 is a schematic diagram of an energy distributing node configured to harvest energy from a structure and to distribute excess energy according to an embodiment of the present invention.
Figure 5:
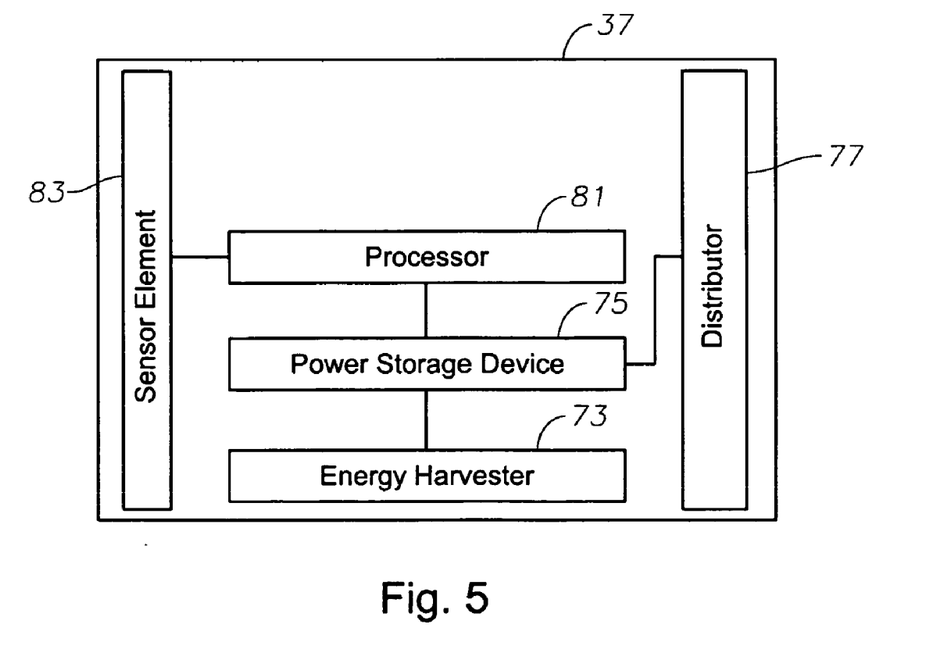
FIG. 5 is a schematic diagram of an energy distributing node as shown in FIG. 4 also configured to sense parameters of a structure according to an embodiment of the present invention.

As shown in FIGS. 4 and 5, the system 30 can also include one or more energy distributing nodes 37 connected to the body 33 of the structure 31, or a portion thereof. The energy distributing nodes 37 can have an energy harvester 73 to harvest energy, an energy storage circuit or device 75 to store harvested energy, and an energy transmitter or distributor 77 positioned/positionable to provide energy through, for example, the body 33 of the structure 31, to a subset of the health monitoring sensor nodes 35. The energy distributing nodes 37 having an energy harvester 73 can be positioned in the area of high environmental energy to thereby obtain environmental energy directly from the body 33 to power the energy distributing node 37 and to convert and distribute excess energy to the health monitoring sensor nodes 35 which may be positioned in the area of low environmental energy. An example configuration can be twenty five health monitoring sensor nodes, five being powered by an external power source, battery, the other twenty nodes obtaining power from environmental energy harvesting and/or the energy distributing node 37, which may or may not itself be powered by environmental energy, a battery, or external power.

Advantageously, depending upon the configuration of the energy distributing nodes 37, the distributed excess energy can be in the form of one of the following types of energy: acoustic energy, radiofrequency energy, electromagnetic energy, optical energy, thermal energy, and vibration energy. As such, the energy transmitter or distributor 77 can include, for example, a piezoelectric transmitter known to those skilled in the art to distribute acoustic and/or vibration energy to the body 33 of the structure 31 as an acoustic or vibratory signal to be harvested and converted to electrical energy by one or more adjacent health monitoring sensor nodes 35, to thereby provide power to the sensor nodes 35. Note, the energy distributing node 37 can harvest vibrations at one frequency and transmit or otherwise distribute vibrations in other frequency where the transmission properties of the material is more permissive to that other frequency. Similarly, the energy distributing node 37 can harvest energy in a first form and distribute at least a portion of the energy in a different form.

The energy transmitter or distributor 77 can include an electromagnetic energy transmitter or device known to those skilled in the art to distribute electromagnetic energy to be harvested and converted to electrical energy by one or more of the health monitoring sensor nodes 35, to thereby provide power to the sensor nodes 35. Similarly, the energy transmitter or distributor 77 can include a radiofrequency transmitter or similar device known to those skilled in the art including, e.g., a combination of an oscillator, output transmitter, and antenna, to distribute radiofrequency energy (form of electromagnetic energy) as a radiofrequency signal to be harvested and converted to electrical energy by one or more of the health monitoring sensor nodes 35, to thereby provide power to the sensor nodes 35. Note, the radiofrequency signal may not be the example 125 kHz ideally utilized in some communication scenarios with embedded health monitoring sensor nodes 35 because the signal may not need to penetrate the aircraft aluminum or composite skin, but rather may have an unobstructed view of the receiver energy health monitoring sensor node 35 via a channel or passageway within the structure 31. That is, advantageously, the communication frequency can be one frequency that provides transmission efficiency, and the energy distribution-harvesting frequency can be another frequency which provides enhanced energy conversion or distribution efficiency.

The energy transmitter or distributor 77 can include an optical transmitter or similar device known to those skilled in the art, e.g., light emitting diode, to distribute optical or light energy as an optical signal to be harvested and converted to electrical energy by one or more of the health monitoring sensor nodes 35, to thereby provide power to the sensor nodes 35. The optical signal can be transmitted directly to the energy harvester 55, e.g., photovoltaic cell, of the health monitoring sensor node 35, can be transmitted through a conductor such as, for example, a fiber optic cable (not shown), or can be reflected or retracted by a portion of the body 33. To reduce complexity, however, it is generally preferred that if implemented with a fiber optic cable, the fiber optic cable not directly connect to the energy harvester 55 or other portion of the health monitoring sensor node 35, but rather conduct the light signal around an obstacle until within view of the energy harvester 55 of the health monitoring sensor node 35, and then terminate.

The energy transmitter or distributor 77 can, for example, include a thermal energy transmitter or similar device known to those skilled in the art, e.g., heating element, to distribute thermal energy to be harvested and converted to electrical energy by one or more of the health monitoring sensor nodes 35, to thereby provide power to the sensor nodes 35.

As shown in FIG. 5, each energy distributing node 37 can also include a processor 81 positioned to manage the distribution of energy. For example, in conjunction with a sensor element 83, the processor 81 can detect parameters of the structure 31, which the processor 81 can utilize as an indication to provide stored and/or currently harvested energy to the distributor 77 for distribution to the various health monitoring sensor nodes 35. This can help prevent undesired depletion of the power stored by the power storage device 75.

Figure 6:
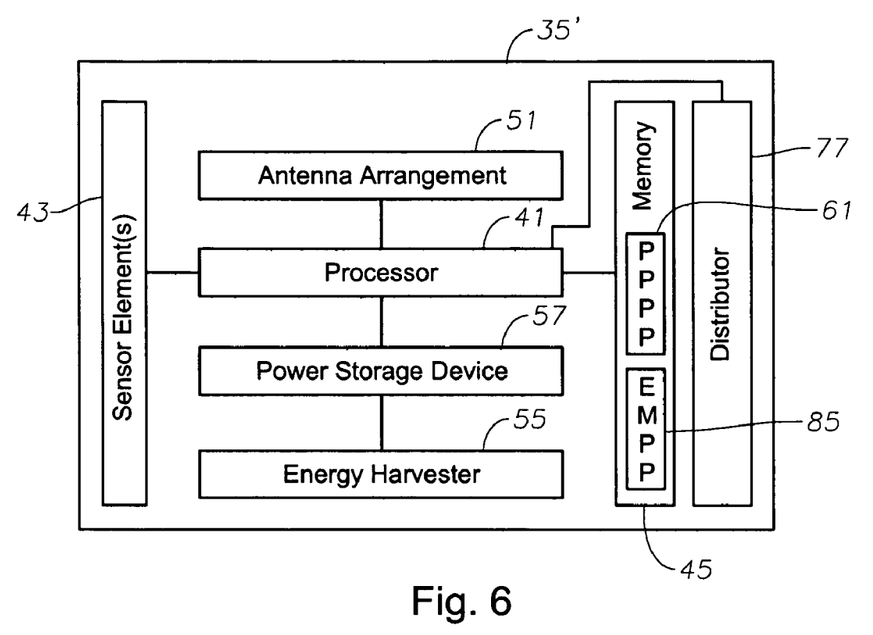
FIG. 6 is a schematic diagram of a health monitoring sensor node configured to sense parameters and to harvesting energy from a structure and to distribute excess energy according to an embodiment of the present invention.

In an alternative embodiment of the present invention, as shown in FIG. 6, one or more of the health monitoring sensor nodes 35' can also include such an energy transmitter or distributor 77 positioned/positionable to provide excess energy through, for example, the body 33 of the structure 31, to adjacent health monitoring sensor nodes 35. Each health monitoring sensor node 35', either through additional hardware known to those skilled in the art (not shown) or through energy monitoring program product 85 preferably stored in the memory 45, can monitor or otherwise determine the amount of excess power available to selectively actuate the energy transmitter or distributor 77. Note, each energy distribution node 77, either through hardware or through the energy product 85 preferably stored in an associated memory (not shown) can also be provided to selectively actuate the energy transmitter or distributor 77.

Figure 7:
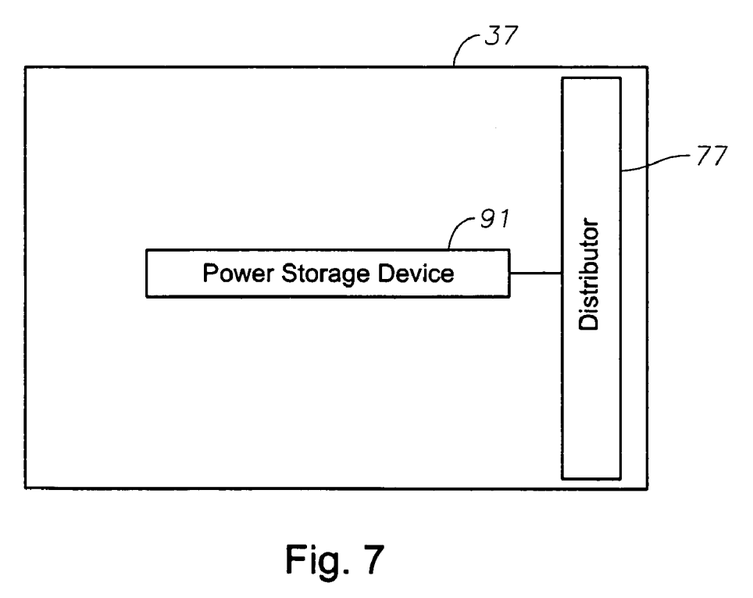
FIG. 7 is a schematic diagram of an energy distributing node configured to distribute excess energy according to an embodiment of the present invention.

As shown in FIG. 7, according to an embodiment of the present invention, the energy distributing node 37 can include a battery or other power storage device 91 capable of independently powering the energy distributing node 37 in place of or in addition to the storage circuit or device 75. Note, the power storage device 91 can include chemical, electrical, thermal, radioactive storage, or other storage means known to those skilled in the art. The chemical storage can include fuel cells, micro-engines, and some types of batteries. The electrical storage can include batteries, ultra-capacitors, and ultra-inductors. The thermal storage can include thermal collectors. The radioactive storage can use direct conversion, beta-voltaic conversion, or thermoelectric conversion.

Figure 8:
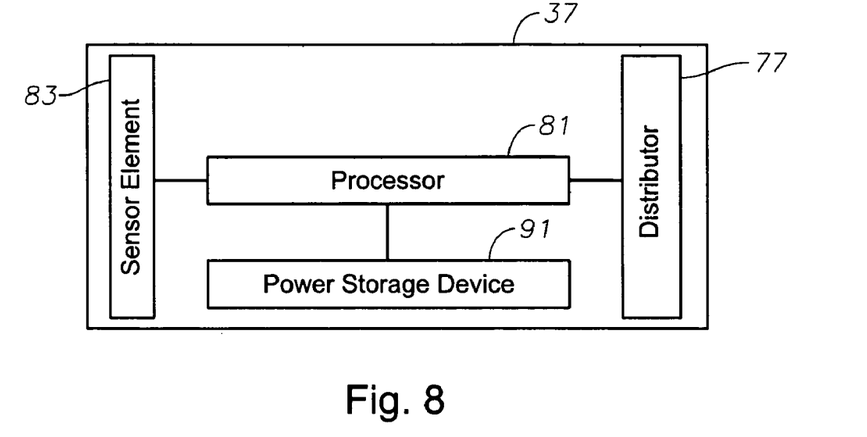
FIG. 8 is a schematic diagram of an energy distributing node as shown in FIG. 7 also configured to sense parameters of a structure according to an embodiment of the present invention.

According to such embodiment, the energy distributing node 37 can obtain energy from the power storage device 91 to power the energy distributing node 37 and to convert and distribute excess energy to the health monitoring sensor nodes 35, 35'. As shown in FIG. 8, the energy distributing node 37 can also include a processor 81 positioned to manage the distribution of that energy. That is, in conjunction with a sensor element 83, the processor 81 can detect parameters of the structure 31, which the processor 81 can utilize as an indication to provide stored and/or currently harvested energy to the distributor 77 for distribution to the various health monitoring sensor nodes 35. Note, the energy harvesting and energy distributing health monitoring sensor node 35' shown in FIG. 6 can also include a battery or other high capacity power storage device in place of or in addition to the energy harvester 55 and/or the storage circuit or device 57. Likewise, the energy distributor node 37 shown in FIG. 5 can include a battery or other high capacity power storage device.

Figure 9:
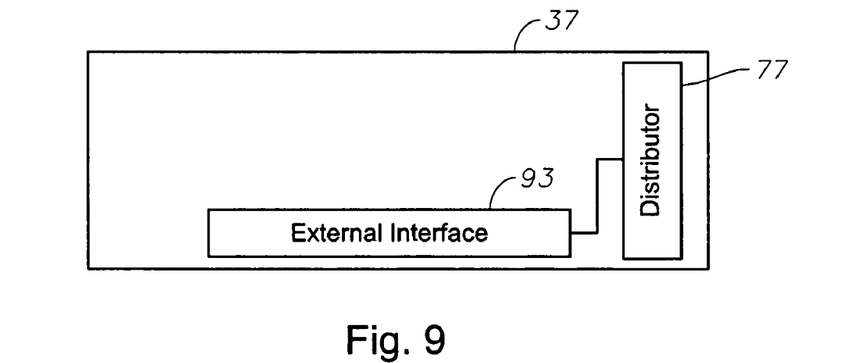
FIG. 9 is a schematic diagram of an energy distributing node configured to distribute excess energy according to an embodiment of the present invention.
Figure 10:
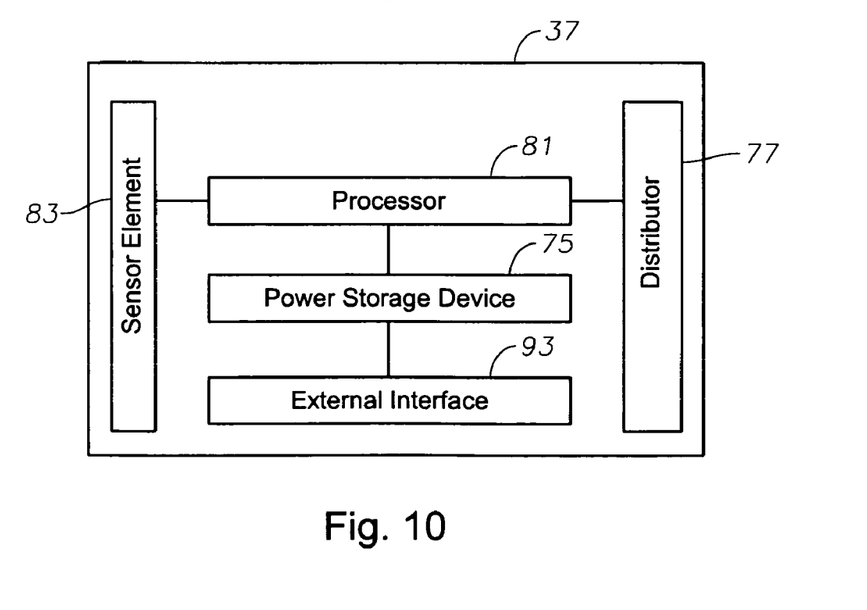
FIG. 10 is a schematic diagram of an energy distributing node as shown in FIG. 9 also configured to sense parameters of a structure according to an embodiment of the present invention.

As shown in FIG. 9, the energy distributing node 37 can include an external interface 93 in place of or in addition to the energy harvester 73 and storage circuit or device 75. According to such embodiment, the energy distributing node 37 can obtain energy from the aircraft power grid (not shown) or other external source to power the energy distributing node 37 and to convert and distribute excess energy to the health monitoring sensor nodes 35, 35'. As shown in FIG. 10, the energy distributing node 37 can also include a processor 81 positioned to manage the distribution of energy and a storage circuit or device 75 to provide uniform power delivery and dampen any power fluctuations. In conjunction with a sensor element 83, the processor 81 can detect parameters of the structure 31, which the processor 81 can utilize as an indication to provide stored and/or currently harvested energy to the distributor 77 for distribution to the various health monitoring sensor nodes 35. Note, the energy harvesting and energy distributing health monitoring sensor node 35' shown in FIG. 6 can also include an external interface 93 in place of or in addition to the energy harvester 55.

According to an embodiment of the present invention, the system 30 includes multiple sets of health monitoring sensor nodes 35, 35', some sets of nodes positioned in areas of high environmental energy with others positioned in areas of relatively low environmental energy. At least one set of the health monitoring sensor nodes 35, 35', is configured and positioned so that at least some of such nodes 35, 35', can harvest sufficient energy by harvesting from the combination of energy from the environment, energy radiated from adjacent health monitoring sensor nodes 35, 35', in the area of high environmental energy, and energy radiated from adjacent health monitoring sensor nodes 35, 35', in the area of low environmental energy. According to an alternative embodiment of the present invention, at least one set of the health monitoring sensor nodes 35, 35', is configured and positioned so that at least some of such nodes 35, 35', can harvest sufficient energy from energy radiated from adjacent health monitoring sensor nodes 35, 35' in the area of high environmental energy and energy radiated from adjacent health monitoring sensor nodes 35, 35' in the area of low environmental energy, without the need to harvest directly from that energy inherently produced by the environment.

Figure 11:
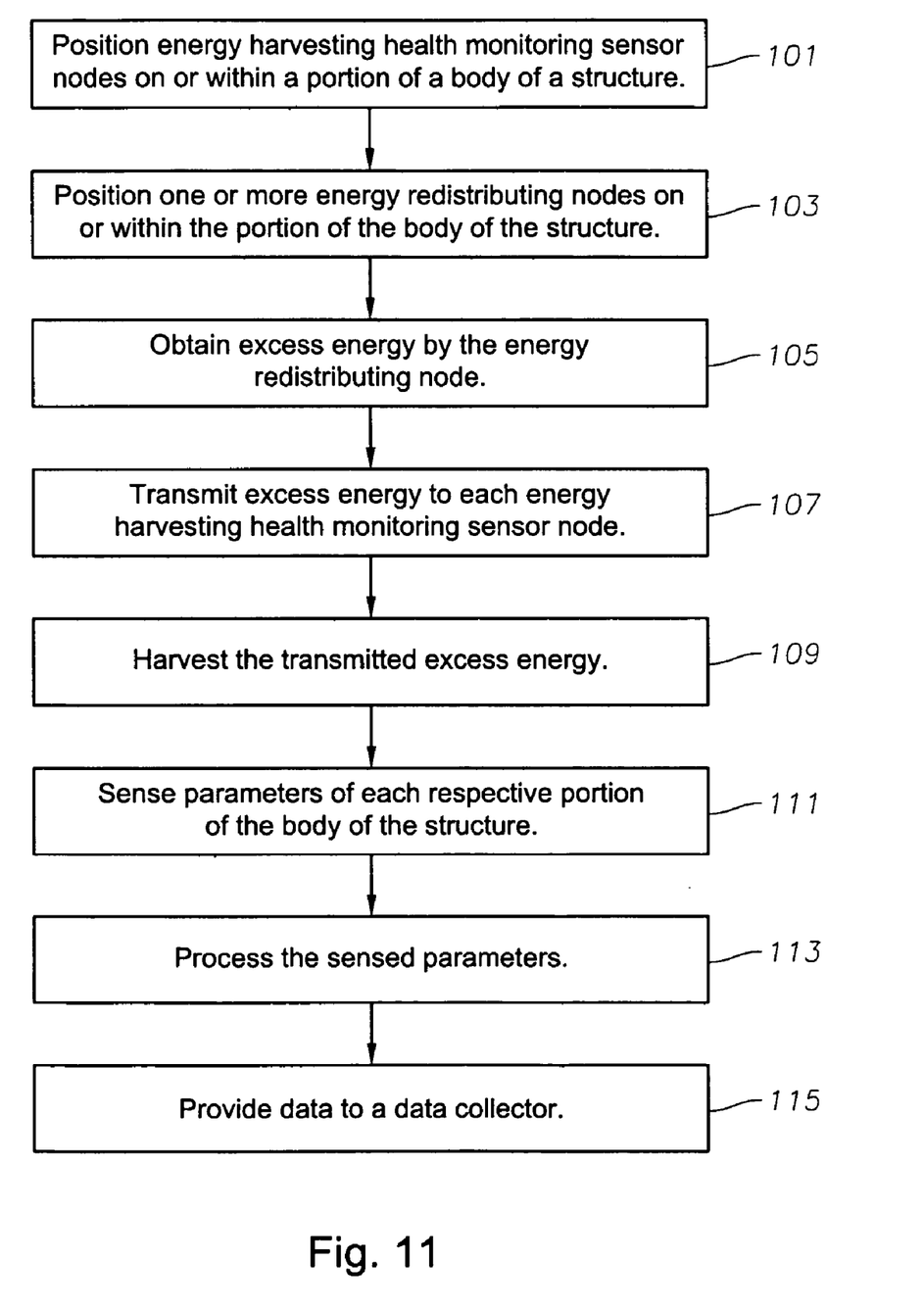
FIG. 11 is a schematic flow diagram of a method of providing energy to a plurality of health monitoring sensor nodes connected to a structure according to an embodiment of the present invention.

As shown in FIGS. 1-11, embodiments of the present invention include methods of providing energy to health monitoring sensor nodes connected to a structure to monitor parameters related to the structure. For example, according to an embodiment of the present invention, as perhaps as shown in FIG. 11, a method includes the step of positioning multiple sets of preferably wireless energy harvesting health monitoring sensor nodes (block 101) such as, for example, health monitoring sensor nodes 35, 35', described previously (see FIGS. 3 and 6) on or within a portion of a body 33 of a structure 31 such as, for example, an aircraft wing or fuselage. The sensor nodes 35, 35', can include a processor 41, a storage device 57 to store excess power interfaced with the processor 41, a sensor or sensor element 43 interfaced or otherwise in communication with the processor 41 to sense parameters of the body 33 of the structure 31, memory 45 interfaced with the processor 41 to store sensed parameter data, and an antenna arrangement 51 interfaced with the processor to receive and provide signals. Some of the nodes 35, 35', are positioned in portions of the structure 31 having insufficient environmental energy to otherwise allow continuous operation of each of the health monitoring sensor nodes 35, 35', while others are positioned in portions of the structure 31 having sufficient available environmental energy. The health monitoring sensor nodes 35, 35' can include an energy harvester 55 in communication or interfaced with the processor 41 and positioned to harvest energy. The energy harvester 55 can include one or more of the following: an acoustic energy harvester, an electromagnetic energy harvester, a radiofrequency energy harvester, an optical energy harvester, a thermal energy harvester, and one or more vibration or mechanical energy harvesters capable of harvesting from separate and distinct frequency ranges. Note, continuous operation can include intermittent powering of the sensor element 43 and processor 41 according to a predetermined energy conservation methodology.

The method also includes the step of positioning on or within a portion of the body 33 of the structure 31, one or more energy distributing nodes (block 103) such as, for example, energy distributing nodes 37, described previously (see, e.g., FIGS. 4, 5, and 7-10). The energy distributing nodes 37 can obtain excess power from various energy sources and interfaces such as, for example, one or more of the following: a high capacity battery or other high capacity storage device 91 (FIG. 7), an external interface 93 (FIG. 9) to extract external power from the structure power grid, and an energy harvester 73 and energy storage device 75 to harvest and store environmental energy. The energy distributing nodes 37 having an energy harvester 73 can be positioned in the area of high environmental energy to thereby obtain environmental energy from or through the body 33 to convert and distribute excess energy to the health monitoring sensor nodes 35, 35', particularly those positioned in the area of low environmental energy. The energy harvester 73 can be positioned to harvest energy provided by mechanical, chemical, heat, solar, or other, means including acoustic energy, radiofrequency energy, electromagnetic energy, optical (light) or solar energy, thermal energy, and vibration energy. As such, the method can also include obtaining and storing excess energy by the energy distributing node 37 (block 105). As described above, the excess energy can be obtained through harvesting energy from the environment, extracting energy from an associated power storage device 91, or interfacing with and drawing power from an external power source such as, for example, the aircraft power grid, via an external interface 93.

The energy distributing nodes 37 can also have an energy transmitter or distributor 77 to transmit/distribute excess energy to the energy harvesting health monitoring sensor nodes 35, 35', which are positioned in the area of low environmental energy. Depending upon the configuration of the energy distributing node 37, as described previously, the distributed excess energy can be in the form of one of the following: acoustic energy, radiofrequency energy, electromagnetic energy, optical energy, thermal energy, and vibration or mechanical energy. As such, the method can also include transmitting or otherwise distributing the excess acoustic, electromagnetic, radiofrequency, optical/light, thermal, and vibration or mechanical energy to adjacent energy harvesting health monitoring sensor nodes 35, 35' (block 107). With respect to vibration, electromagnetic, acoustic, and radiofrequency energy, the energy transmitter or distributor 77 need not provide the energy on the same frequency as that available through environmental or other conditions as long as one or more of the energy harvesters 55 are configured to receive such frequency from the energy distributing node 37. For example, assuming environmental energy is available to a health monitoring sensor node 35, 35', at a first frequency, a first energy harvester 55 can harvest energy from the environment. If a second frequency, however, provides better transmission efficiency, the energy harvester 55 or a separate energy harvester 55 of the node 35, 35', and the energy transmitter or distributor 77 of one or more adjacent energy distribution nodes 37 can be configured to the second more transmission efficient frequency.

The adjacent health monitoring sensor nodes 35, 35', can harvest the transmitted or distributed excess energy (block 109) to thereby provide power to the nodes 35, 35', to sense parameters of the respective portion of the body 33 of the structure 31 (block 111), and process the sensed parameters (block 113). The method can further include providing data to data collectors (block 115), e.g., data collectors or interrogators 39, either after the structure 31 has been subjected to various environmental conditions affecting the health of the structure 31 or during exposure to such environmental conditions. In the aircraft example, this step can be performed automatically during flight or during ground operations through use of, for example, a central processor 40 (FIG. 1), if the data collectors 39 are prepositioned within communication range of the health monitoring sensor nodes 35, 35'. This step can be performed semi-automatically if the data collectors 39 are positioned at a fixed location such as, for example, on a hangar gate or at the aircraft parking area or taxi location, to thereby "read" the sensors as the aircraft is passed by a position within range of the data collectors 39. This step can alternatively be performed manually by maintenance personnel passing a hand-held version of the data collectors 39 within communication range of the nodes 35, 35'.

It is important to note that while embodiments of the present invention have been described in the context of a fully functional system, those skilled in the art will appreciate that the mechanism of the present invention and/or aspects thereof are capable of being distributed in the form of a computer readable medium of instructions in a variety of forms for execution on a processor, processors, or the like, and that the present invention applies equally regardless of the particular type of signal bearing media used to actually carry out the distribution. Examples of computer readable media include but are not limited to: nonvolatile, hard-coded type media such as read only memories (ROMs), CD-ROMs, and DVD-ROMs or erasable, electrically programmable read only memories (EEPROMs), recordable type media such as floppy disks, hard disk drives, CD-R/RWs, DVD-RAMs, DVD-R/RWs, DVD+R/RWs, flash drives, and other newer types of memories, and transmission type media such as digital and analog communication links. For example, such media can include both operating instructions and instructions related to the parameter processing program product 61, the energy monitoring program product 85, and the processor related method steps described above.

The invention has several advantages. Embodiments of the present invention combine conventional energy harvesting with means to transfer additional energy from nodes that have excess energy to ones that have less energy. A combination of power harvesting and radiated power enables wireless power distribution in a multi-node system. Advantageously, power is made available to those nodes that may not be in an optimum location for environmental energy harvesting, thus providing better utilization of available power by sharing power between nodes with excess available power and nodes with insufficient power. Embodiments of the present invention provide a special energy radiating node which can be positioned in a location with high levels of available energy. This node can transfer energy to neighboring nodes thorough one of various methods: acoustic, radio frequency, electromagnetic, optical or thermal. Advantageously, according to embodiments of the present invention, the energy radiating nodes also have an energy harvester, and a method or means to convert excess energy to one of the aforementioned radiated energy forms. Neighboring nodes can harvest the radiated energy, and can supplement or completely rely on that energy to perform their function. Advantageously, according to various embodiments of the present invention, all nodes can have the capability of harvesting energy, as well as converting excess energy to a form that is radiated to neighboring nodes. Nodes that are in a high-energy environment can harvest the needed energy to perform their function, and radiate the excess energy to their neighboring nodes. Nodes that are in a low energy environment can supplement their available energy though the radiated energy from neighboring nodes. Each node can have energy harvesting components that are able to collect energy from the environment, their neighboring nodes, or from the special energy radiating node. Advantageously, the special energy radiating node is powered via energy harvesting components, uses a battery for power, and/or directly connected to the power grid of the system or structure, which it monitors. Advantageously, the implementation of the sensor nodes can be quite versatile. In one embodiment, the sensor nodes can harvest power from the environment as well as the radiated energy. In another embodiment, the sensor nodes can harvest power solely from the radiated energy source.

In the drawings and specification, there have been disclosed a typical preferred embodiment of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification. For example, various other circuit designs known to those skilled in the art can be utilized to harvest and/or store energy obtained from the environment and are within the scope of the present invention.

This invention is related to Non-Provisional application Ser. No. 11/289,795, by Andarawis, et al., titled "System to Monitor the Health of a Structure, Sensor Nodes, Program Product, and Related Methods," filed on Nov. 23, 2005, and Non-Provisional application Ser. No. 11/286,792, by Andarawis, et al., titled "System to Monitor the Health of a Structure, Sensor Nodes, Program Product, and Related Methods," filed on Nov. 23, 2005, all incorporated by reference herein in their entirety.

The invention claimed is:

1. A system to monitor the health of a structure, the system comprising:
   a structure to be monitored having a body;
   at least one wireless energy harvesting apparatus connected to the body of the structure and positioned to monitor and transmit parameters of a portion of the body of the structure, the at least one wireless energy harvesting apparatus configured to harvest energy to supply electrical power thereto; and
   an energy distributing apparatus connected to the body of the structure separate from the at least one energy harvesting apparatus and having a wireless energy transmitter positioned to provide energy to the at least one wireless energy harvesting apparatus.

2. The system as defined in claim 1,
   wherein the body of the structure when in operation includes a first area having a first level of environmental energy to define an area of high environmental energy and a second area having a second level of environmental energy to define an area of low environmental energy, the first area spaced apart from the second area, a mean of the first level of environmental energy substantially greater than a mean of the second level of environmental energy;
   wherein each of the at least one energy harvesting apparatus is positioned in the area of low environmental energy;
   wherein the energy distributing apparatus includes an energy harvester to harvest energy; and
   wherein the energy distributing apparatus is positioned in the area of high environmental energy to thereby harvest environmental energy from the body to power the energy distributing apparatus and to convert and distribute excess energy to the at least one energy harvesting apparatus positioned in the area of low environmental energy.

3. The system as defined in claim 1,
   wherein the energy distributing apparatus includes a power storage device;
   wherein the energy distributing apparatus is powered by the power storage device; and
   wherein the energy distributing apparatus is adapted to obtain energy from the power storage device to power the energy distributing apparatus and to convert and distribute excess energy to the at least one energy harvesting apparatus, the distributed excess energy in the form of one of the following types of energy: acoustic energy, radiofrequency energy, electromagnetic energy, optical energy, thermal energy, and vibration energy.

4. The system as defined in claim 1,
   wherein the structure includes a portion of an aircraft having an aircraft power grid;
   wherein the energy distributing apparatus is powered by the aircraft power grid; and
   wherein the energy distributing apparatus is adapted to obtain energy from the aircraft power grid to power the energy distributing apparatus and to convert and distribute excess energy to the at least one energy harvesting apparatus, the distributed excess energy in the form of one of the following types of energy: acoustic energy, radiofrequency energy, electromagnetic energy, optical energy, thermal energy, and vibration energy.

5. The system as defined in claim 1,
   wherein the energy distributing apparatus is powered by an energy source having a first energy form; and
   wherein the energy distributing apparatus is adapted to obtain energy from the energy source to power the energy distributing apparatus and to convert and distribute excess energy to the at least one energy harvesting apparatus, the distributed excess energy having a second energy form.

6. The system as defined in claim 1,
   wherein the energy distributing apparatus provides acoustic energy as an acoustic signal to a portion of the body of the structure to thereby transfer acoustic energy to the at least one energy harvesting apparatus; and
   wherein the at least one energy harvesting apparatus includes an acoustic energy harvester positioned to harvest a portion of the acoustic signal to convert the harvested portion of the acoustic signal to electrical energy to thereby provide power to the energy harvesting apparatus.

7. The system as defined in claim 1,
   wherein the energy distributing apparatus provides radiofrequency energy as a radiofrequency signal to the at least one energy harvesting apparatus to thereby transfer radiofrequency energy to the at least one energy harvesting apparatus; and
   wherein the at least one energy harvesting apparatus includes a radiofrequency energy harvester positioned to harvest a portion of the radio frequency signal from the energy distributing apparatus to convert the harvested portion of the radiofrequency signal to electrical energy to thereby provide power to the energy harvesting apparatus.

8. The system as defined in claim 1,
wherein the energy distributing apparatus provides electromagnetic energy to the at least one energy harvesting apparatus to thereby transfer energy to the at least one energy harvesting apparatus; and
wherein the at least one energy harvesting apparatus includes an electromagnetic energy harvester positioned to harvest a portion of the electromagnetic energy from the energy distributing apparatus to convert the harvested portion of the electromagnetic energy to electrical energy to thereby provide power to the energy harvesting apparatus.

9. The system as defined in claim 1,
wherein the at least one energy harvesting apparatus has an optical pathway to a portion of the energy distributing apparatus;
wherein the energy distributing apparatus provides optical energy as an optical signal to the at least one energy harvesting apparatus to thereby transfer energy to the at least one energy harvesting apparatus; and
wherein each of the at least one energy harvesting apparatus includes an optical energy harvester positioned to harvest a portion of the optical signal from the energy distributing apparatus to convert the harvested portion of the optical signal to electrical energy to thereby provide power to the energy harvesting apparatus.

10. The system as defined in claim 1,
wherein the energy distributing apparatus provides thermal energy to a portion of the body of the structure to thereby transfer thermal energy to the at least one energy harvesting apparatus; and
wherein each of the at least one energy harvesting apparatus include a thermal energy harvester positioned to harvest a portion of the thermal energy from the energy distributing apparatus to convert the harvested portion of the thermal energy to electrical energy to thereby provide power to the energy harvesting apparatus.

11. The system as defined in claim 1,
wherein the energy distributing apparatus provides vibration energy to a portion of the body of the structure to thereby transfer vibration energy to the at least one energy harvesting apparatus; and
wherein each energy harvesting apparatus of the at least one energy harvesting apparatus includes a vibration energy harvester positioned to harvest a portion of the vibration energy to convert the harvested portion of the vibration energy to electrical energy to thereby provide power to the energy harvesting apparatus.

12. The system as defined in claim 1,
wherein the system includes an interrogator having an antenna arrangement positioned to provide a signal indicative of a request for data from the at least one energy harvesting apparatus and to receive requested data therefrom; and
wherein the at least one energy harvesting apparatus includes a first antenna positioned to receive the signal from and provide data to the interrogator and having a first preselected resonant frequency tuned to provide for substantial transmission energy efficiency, and a second antenna positioned to harvest energy and having a second preselected resonant frequency tuned to provide for substantial energy conversion efficiency, the second preselected resonant frequency selected based upon a material composition of the body of the structure, the energy conversion efficiency dependent upon the material composition of the body of the structure.

13. The system as defined in claim 1,
wherein the system includes an interrogator having a transmitter arrangement positioned to provide a signal indicative of a request for data from the at least one energy harvesting apparatus and to receive requested data therefrom; and
wherein the at least one energy harvesting apparatus includes a first receiver arrangement positioned to receive the signal from and provide data to the interrogator and having a first preselected receive frequency to provide for substantial transmission energy efficiency, and a second receiver arrangement positioned to harvest energy and having a second preselected receive frequency spaced apart from that of the first preselected receive frequency to provide for substantial energy conversion efficiency, the second preselected receive frequency selected based upon a material composition of the body of the structure, the energy conversion efficiency dependent upon the material composition of the body of the structure.

14. The system as defined in claim 1,
wherein the system includes an interrogator having an optical transmitter arrangement positioned to provide an optical signal indicative of a request for data from the at least one energy harvesting apparatus and to receive requested data therefrom; and
wherein the at least one energy harvesting apparatus includes a first optical receiver positioned to receive the optical signal from and provide data to the interrogator and having a first preselected frequency, and a second optical receiver positioned to harvest energy and having a second preselected frequency spaced apart from that of the first preselected receive frequency, the second preselected frequency providing different scatter properties than the first preselected frequency.

15. A multi-node sensor system to monitor the health of a structure, the system comprising:
a structure to be monitored having a body including both a first area having a first level of environmental energy to define an area of high environmental energy and a second area having a second level of environmental energy to define an area of low environmental energy when in operation, the first area spaced apart from the second area, a mean of the first level of environmental energy substantially greater than a mean of the second level of environmental energy;
a plurality of separate wireless energy harvesting structural health monitoring sensor nodes each connected to or embedded within the body of the structure to monitor structural health of a portion of the body of the structure and positioned in the area of low environmental energy; and
an energy distributing node connected to the body of the structure, having an energy harvester to harvest energy and a wireless energy transmitter to provide energy through the body of the structure to each of the plurality of energy harvesting structural health monitoring sensor nodes, and positioned in the area of high environmental energy to thereby obtain environmental energy from the body to power the energy distributing node and to convert and distribute excess energy through the body of the structure to the plurality of energy harvesting health monitoring sensor nodes positioned in the area of low environmental energy.

16. The system as defined in claim 15,
wherein the plurality of energy harvesting health monitoring sensor nodes is a first plurality of energy harvesting health monitoring sensor nodes;

wherein each of the first plurality of energy harvesting health monitoring sensor nodes is also an energy distributing node;

wherein the system includes a second plurality of energy harvesting health monitoring sensor nodes, each also an energy distributing node;

wherein the second plurality of energy harvesting health monitoring sensor nodes is positioned in the area of high environmental energy; and wherein each of the first plurality of health monitoring sensor nodes is positioned to harvest energy from the environment, energy radiated from adjacent ones of the first plurality of health monitoring sensor nodes, and energy radiated from adjacent ones of the second plurality of health monitoring sensor nodes.

17. The system as defined in claim 15, wherein the plurality of energy harvesting health monitoring sensor nodes is a first plurality of energy harvesting health monitoring sensor nodes;

wherein each of the first plurality of energy harvesting health monitoring sensor nodes is also an energy distributing node;

wherein the system includes a second plurality of energy harvesting health monitoring sensor nodes, each also an energy distributing node;

wherein the second plurality of energy harvesting health monitoring sensor nodes is positioned in the area of high environmental energy; and wherein each of the first plurality of energy harvesting health monitoring sensor nodes is positioned to harvest energy from that radiated from adjacent ones of the first plurality of energy harvesting health monitoring sensor nodes and that radiated from adjacent ones of the second plurality of energy harvesting health monitoring sensor nodes, and not directly from that inherently produced by the environment.

18. The system as defined in claim 15, wherein the energy distributing node distributes energy having a first form;

wherein each sensor node of the plurality of energy harvesting health monitoring sensor nodes includes a processor, a storage device to store excess power interfaced with the processor, a sensor to sense parameters of the body of the structure interfaced with the processor, memory interfaced with the processor to store sensed parameter data, a communication arrangement interfaced with the processor to receive and provide data signals, and a first energy harvester interfaced with the processor and positioned to harvest environmental energy having a second form from the body of the structure to convert the harvested vibration energy to electrical energy to thereby provide power for the sensor node; and wherein at least one sensor node of the plurality of energy harvesting health monitoring sensor nodes also includes a second energy harvester interfaced with the processor and positioned to harvest energy distributed from the energy distributing node having the first form.

19. The system as defined in claim 18, wherein the first form of energy includes at least one of the following types of energy: acoustic energy, radiofrequency energy, electromagnetic energy, optical energy, thermal energy, and vibration energy;

wherein the first energy harvester includes a vibration energy harvester positioned to harvest environmental vibration energy from the body of the structure having a first frequency range to convert the harvested vibration energy to electrical energy to thereby provide power for the sensor node; and wherein the second energy harvester includes at least one of the following:

an acoustic energy harvester positioned to harvest acoustic energy distributed to the body of the structure by the energy distributing node as an acoustic signal to convert the harvested acoustic energy to electrical energy to thereby provide power to the sensor node, a radiofrequency energy harvester positioned to harvest radio frequency energy distributed from the energy distributing node as a radiofrequency signal to convert the harvested radiofrequency energy to electrical energy to thereby provide power to the sensor node, an electromagnetic energy harvester positioned to harvest electromagnetic energy distributed from the energy distributing node to convert the harvested portion of the electromagnetic energy to electrical energy to thereby provide power to the sensor node, an optical energy harvester positioned to harvest optical energy distributed from the energy distributing node to convert the harvested portion of the optical signal to electrical energy to thereby provide power to the sensor node, a thermal energy harvester positioned to harvest thermal energy distributed from the energy distributing node to convert the harvested portion of the thermal energy to electrical energy to thereby provide power to the sensor node, and a vibration energy harvester positioned to harvest a portion of the vibration energy distributed from the energy distributing node and having a second frequency range to convert the harvested portion of the vibration energy to electrical energy to thereby provide power to the sensor node.

20. The system as defined in claim 18, wherein the first form of energy includes at least one of the following types of energy: acoustic energy, radiofrequency energy, electromagnetic energy, optical energy, thermal energy, and vibration energy;

wherein the first energy harvester includes a thermal energy harvester positioned to harvest environmental thermal energy from the body of the structure to convert the harvested thermal energy to electrical energy to thereby provide power for the sensor node; and wherein the second energy harvester includes at least one of the following:

an acoustic energy harvester positioned to harvest acoustic energy distributed to the body of the structure by the energy distributing node as an acoustic signal to convert the harvested acoustic energy to electrical energy to thereby provide power to the sensor node, a radiofrequency energy harvester positioned to harvest radio frequency energy distributed from the energy distributing node as a radiofrequency signal to convert the harvested radiofrequency energy to electrical energy to thereby provide power to the sensor node, an electromagnetic energy harvester positioned to harvest electromagnetic energy distributed from the energy distributing node to convert the harvested portion of the electromagnetic energy to electrical energy to thereby provide power to the sensor node, an optical energy harvester positioned to harvest optical energy distributed from the energy distributing node to convert the harvested portion of the optical signal to electrical energy to thereby provide power to the sensor node, and
a vibration energy harvester positioned to harvest a portion of the vibration energy distributed from the energy distributing node to convert the harvested portion of the vibration energy to electrical energy to thereby provide power to the sensor node.

21. The system as defined in claim 15,
wherein the plurality of energy harvesting health monitoring sensor nodes is a first plurality of energy harvesting health monitoring sensor nodes;
wherein the system also includes a second plurality of energy harvesting health monitoring sensor nodes each positioned to monitor health of another portion of the body of the structure to thereby form an array of energy harvesting health monitoring sensor nodes to monitor the health of the body of the structure;
wherein the energy distributing node is a first energy distributing node; and
wherein the system also includes a second energy distributing node connected to the body of the structure having an energy transmitter to provide energy through the body of the structure to each of the second plurality of energy harvesting health monitoring sensor nodes to thereby form an array of energy distributing nodes to provide energy to each of the first and the second plurality of energy harvesting health monitoring sensor nodes.

22. The system as defined in claim 21,
wherein the structure is a wing of an aircraft; and
wherein the system includes an interrogator apparatus positioned within the aircraft and in data communication with:
a first data collector connected to the wing and positioned adjacent a first subset of the first and second plurality of energy harvesting health monitoring sensor nodes to provide a signal indicative of a request for data from the first subset of energy harvesting health monitoring sensor nodes and to receive requested data therefrom, and
a second data collector connected to the wing separate and spaced apart from the first antenna and positioned adjacent a second subset of the first and second plurality of energy harvesting health monitoring sensor nodes to provide a signal indicative of a request for data from the second subset of energy harvesting health monitoring sensor nodes and to receive requested data therefrom.

23. A method of providing energy to health monitoring sensor nodes connected to a structure, the method comprising the steps of:
positioning a plurality of separate wireless energy harvesting health monitoring sensor nodes on or within a first portion of a body of a structure having insufficient environmental energy to allow desired operation of each of the plurality of energy harvesting health monitoring sensor nodes defining an area of low environmental energy;
positioning an energy distributing node on or within a second portion of the body of the structure, the energy distributing node having a wireless energy transmitter to transmit excess energy to each of the plurality of energy harvesting structural health monitoring sensor nodes positioned in the area of low environmental energy; and
transmitting excess energy to each of the plurality of energy harvesting structural health monitoring sensor nodes by the energy distributing node to thereby provide energy to each of the plurality of energy harvesting health monitoring sensor nodes to allow for desired operation of each of the plurality of energy harvesting health monitoring sensor nodes during a preselected phase of activity of the structure.

24. The method as defined in claim 23,
wherein the step of positioning the energy distributing node on or within a portion of the body of the structure includes positioning the energy distributing node on or within a portion of the body of the structure having excess environmental energy necessary to allow substantially continuous operation of the energy distributing node during the preselected phase of activity of the structure;
wherein the energy distributing node includes an energy harvester to harvest environmental energy; and
wherein the method further comprises the step of harvesting energy with the energy harvester of the energy distributing node to thereby obtain environmental energy from the body to power the energy distributing node and to convert and distribute excess energy to each of the plurality of energy harvesting health monitoring sensor nodes positioned in the area of low environmental energy.

25. The method as defined in claim 23, further comprising the steps of:
providing acoustic energy as an acoustic signal to a portion of the body of the structure to thereby transfer acoustic energy to each of the plurality of energy harvesting health monitoring sensor nodes; and
harvesting a portion of the acoustic signal by each respective one of the plurality of energy harvesting health monitoring sensor nodes to convert the harvested portion of the acoustic signal to electrical energy to thereby provide power to each respective one of the plurality of energy harvesting health monitoring sensor nodes.

26. The method as defined in claim 23, further comprising the steps of:
providing radiofrequency energy as a radiofrequency signal to the plurality of energy harvesting health monitoring sensor nodes to thereby transfer radiofrequency energy to each of the plurality of energy harvesting health monitoring sensor nodes; and
harvesting a portion of the radiofrequency signal by each respective one of the plurality of energy harvesting health monitoring sensor nodes to convert the harvested portion of the radiofrequency signal to electrical energy to thereby provide power to each respective one of the plurality of energy harvesting health monitoring sensor nodes.

27. The method as defined in claim 23, further comprising the steps of:
providing electromagnetic energy to the plurality of energy harvesting health monitoring sensor nodes to thereby transfer energy to each of the plurality of energy harvesting health monitoring sensor nodes; and
harvesting a portion of the electromagnetic energy by each respective one of the plurality of energy harvesting health monitoring sensor nodes to convert the harvested portion of the electromagnetic energy to electrical energy to thereby provide power to each respective one of the plurality of energy harvesting health monitoring sensor nodes.

28. The method as defined in claim 23, further comprising the steps of:
providing light energy as an optical signal to the plurality of energy harvesting health monitoring sensor nodes to thereby transfer energy to each of the plurality of energy harvesting health monitoring sensor nodes; and
harvesting a portion of the optical signal by each respective one of the plurality of energy harvesting health monitoring sensor nodes to convert the harvested portion of the optical signal to electrical energy to thereby provide power to each respective one of the plurality of energy harvesting health monitoring sensor nodes.

29. The method as defined in claim 23, further comprising the steps of:
providing thermal energy to a portion of the body of the structure to thereby transfer thermal energy to each of the plurality of energy harvesting health monitoring sensor nodes; and
harvesting a portion of the thermal energy by each respective one of the plurality of energy harvesting health monitoring sensor nodes to convert the harvested portion of the thermal energy to electrical energy to thereby provide power to each respective one of the plurality of energy harvesting health monitoring sensor nodes.

30. The method as defined in claim 23, further comprising the steps of:
providing vibration energy to a portion of the body of the structure to thereby transfer vibration energy to each of the plurality of health monitoring sensor nodes; and
harvesting a portion of the vibration energy by each respective one of the plurality of energy harvesting health monitoring sensor nodes to convert the harvested portion of the vibration energy to electrical energy to thereby provide power to each respective one of the plurality of energy harvesting health monitoring sensor nodes.

* * * * *